United States Patent [19]

Temple, Jr.

[11] 4,423,049

[45] Dec. 27, 1983

[54] 2-[4-[(4,4-DIALKYL-2,6-PIPERIDINEDION-1-YL)BUTYL]-1-PIPERAZINYL]PYRIMIDINES

[75] Inventor: Davis L. Temple, Jr., Evansville, Ind.

[73] Assignee: Mead Johnson & Company, Evansville, Ind.

[21] Appl. No.: 334,688

[22] Filed: Dec. 28, 1981

[51] Int. Cl.$^3$ .................. A61K 31/505; C07D 403/04
[52] U.S. Cl. .................... 424/251; 544/230; 544/231; 544/298; 544/299; 544/309; 544/319; 544/360; 544/389; 546/243
[58] Field of Search .................. 544/295; 424/251

[56] References Cited

U.S. PATENT DOCUMENTS

| | | | |
|---|---|---|---|
| 3,398,151 | 8/1968 | Wu et al. | 424/250 |
| 3,717,634 | 2/1973 | Wu et al. | 544/295 |
| 3,907,801 | 9/1975 | Wu et al. | 544/295 |
| 3,976,776 | 8/1976 | Wu et al. | 424/251 |
| 4,182,763 | 1/1980 | Casten et al. | 424/251 |

FOREIGN PATENT DOCUMENTS 2023594  1/1980  United Kingdom .

OTHER PUBLICATIONS

Wu et al., "Journal Medicinal Chemistry", vol. 15, (5), 1972, pp. 477–479.
Wu et al., "J. Med. Chem.", vol. 12, (4), 1969, pp. 876–881.
Pollard et al., "J. Org. Chem.", vol. 24, (6), 1959, pp. 764–767.
Benica et al., "J. Amer. Pharm. Assoc.", 1950, pp. 451–456.

*Primary Examiner*—Donald G. Daus
*Assistant Examiner*—James H. Turnipseed
*Attorney, Agent, or Firm*—Richard P. Ryan; Robert H. Uloth

[57] ABSTRACT

1-[4-(4,4-Dialkyl-2,6-piperidinedion-1-yl)butyl]piperazines with 2-pyrimidyl substituents in the 4- position have been synthesized and demonstrate useful anxiolytic properties. The compound 4,4-dimethyl-1-[4-[4-(2-pyrimidinyl)-1-piperazinyl]butyl]-2,6-piperidinedione, which has selective anxiolytic activity, constitutes the preferred embodiment of the invention.

12 Claims, No Drawings

2-[4-[(4,4-DIALKYL-2,6-PIPERIDINEDION-1-YL)BUTYL]-1-PIPERAZINYL]PYRIMIDINES

BACKGROUND OF THE INVENTION

Related art can be generalized by compounds of the following structural type:

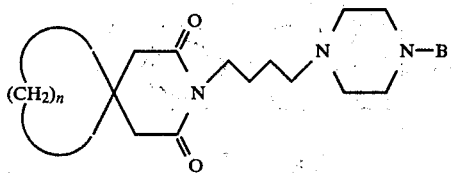

in which n is 4 or 5 and B is a substituted or unsubstituted 2-pyrimidyl moiety. These and related compounds have been prepared as psychotropic agents and are described in:

Wu, et al., *Journal of Medicinal Chemistry*, 15/5, 477-479 (1972).

Wu, et al., U.S. Pat. No. 3,717,634 patented Feb. 20, 1973.

Wu, et al., U.S. Pat. No. 3,907,801 patented Sept. 23, 1975.

Wu, et al., U.S. Pat. No. 3,976,776 patented Aug. 24, 1976.

Anxiolytic use of one of the above compounds (n=4, B=2-pyrimidyl) which is referred to by the name buspirone, is disclosed by Casten, et al., U.S. Pat. No. 4,182,763 patented Feb. 8, 1980. Currently, clinical studies to support a submission to U.S. Food & Drug Administration for the use of buspirone in treatment of anxiety neurosis are being conducted.

Another related group of compounds, including some glutarimides but wherein the B substituent is phenyl or substituted phenyl, is disclosed in:

Wu, et al., U.S. Pat. No. 3,398,151 patented Aug. 20, 1968.

Wu, et al., *Journal of Medicinal Chemistry*, 12/4, 876-881 (1969).

Of increasing dissimilarity are the compounds of the following structure disclosed by Najer, H., et al., in UK Patent Application No. 7,921,307, published as GB No. 2,023,594A on Jan. 3, 1980.

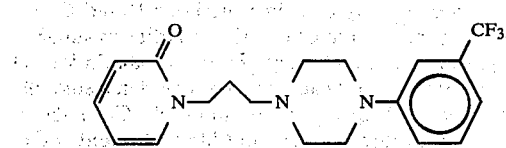

These CNS active compounds are described as being useful in treatment of anxiety and depression.

A piperidyl compound of the following structure was reported by Pollard, et al., in *The Journal of Organic Chemistry*, 24/6, 764-767 (1959); but no utility was given.

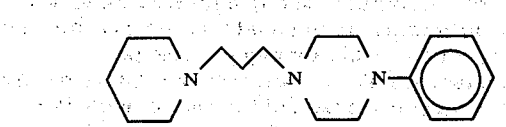

Finally, related but not closely, are some 3,3-dialkylglutarimides as shown in the following structure and reported by Benica, et al., *Journal of the American Pharmaceutical Association*, 1950, 451-456.

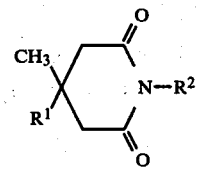

where $R^1$ is $C_1$ to $C_4$ alkyl and $R^2$ is H or $C_1$ to $C_4$ alkyl. Pharmcological testing of these glutarimides did not reveal any useful physiological activity of significance.

As described in the references cited hereinabove, buspirone has a biological profile of a clinically effective anxiolytic agent. However, in certain biological models such as $^3$H-spiperone binding studies and apomorphine stereotypy inhibition, buspirone gives results indicative of neuroleptic or antipsychotic activity. Consequently, an object of the instant invention has been to discover a series of more selective CNS-active compounds; i.e. compounds devoid of neuroleptic activity but which otherwise retain buspirone's novel anxiolytic profile.

SUMMARY OF THE INVENTION

This invention is concerned with a new series of CNS-active compounds characterized by the following general structural formula (I)

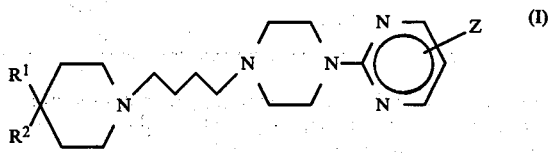

and the non-toxic pharmaceutically acceptable acid addition salts thereof. In the foregoing formula $R^1$ and $R^2$ are independently selected from $C_1$ to $C_4$ alkyl groups; and Z is hydrogen; hydroxyl; halogen, or pseudohalogen; preferably fluoro, chloro, or trifluoromethyl.

The instant compounds differ most notably from buspirone and its related analogs in that their spiroalkylene moiety has been replaced by geminal dialkyl groups.

Testing in biological model systems have shown the compounds of the instant invention to lack activity, compared to related spiro-analogs, in in vitro binding and behavioral tests predictive of antipsychotic activity but to otherwise retain buspirone's unique anxiolytic profile of action.

DETAILED DESCRIPTION OF THE INVENTION

A unitary process comprehending several method embodiments (A, B and C) may be employed for preparation of compounds of Formula I. These methods may be adapted to variation in order to produce other compounds embraced by this invention but not specifically disclosed. Variations of the methods to produce the same compounds in somewhat different fashion will also be evident to one skilled in the art. Certain examples will be given for specific illustration.

Unitary Process

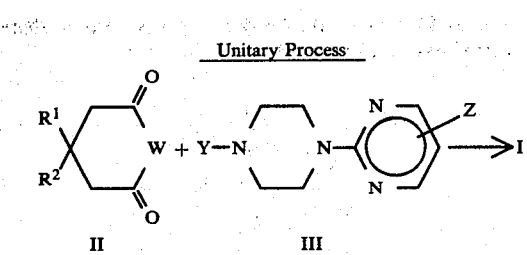

In this scheme, $R^1$, $R^2$, and Z have the same meanings as previously assigned to them in Formula I. The symbol "W" can be $>O$; $>NH$; or $>-(CH_2)_4-X$. The symbol "Y" can be $H_2N-(CH_2)_4-$; $X-(CH_2)_4-$;

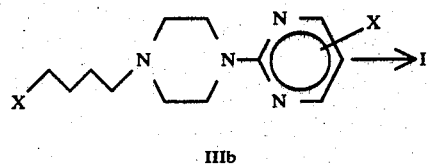

or H. The relationship between W and Y is:

| Method No. | A | B | C |
|---|---|---|---|
| when W is: | $>O$ (IIa) | $>NH$ (IIb) | $>N-(CH_2)_4-X$ (IIc) |
| then Y is: | $H_2N-(CH_2)_4-$ (IIIa) | $X-(CH_2)_4-$ or $\begin{array}{c}X^\ominus\end{array}$ (IIIb) (IIIb') | H (IIIc) |

The symbol "X" refers to a suitable displacement group such as chloride, bromide, iodide, sulfate, phosphate, tosylate, or mesylate.

Method A

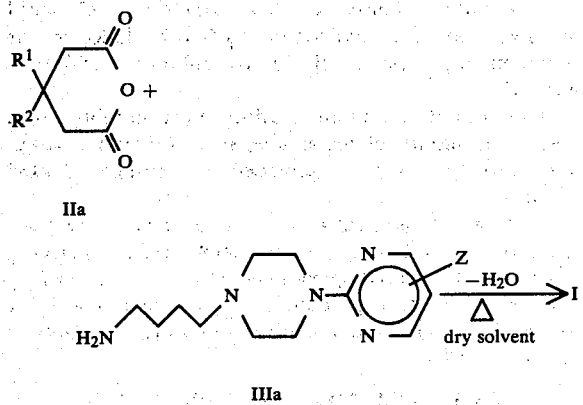

Method B

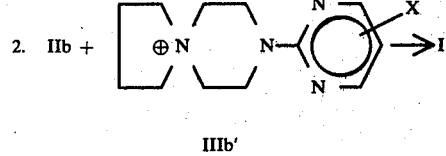

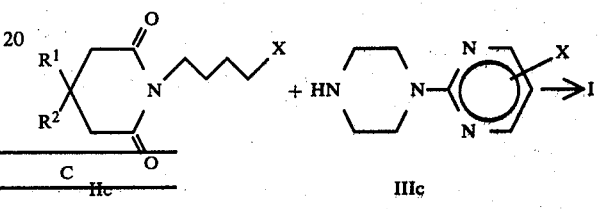

The condensation process in Method A is carried out by refluxing the reactants in a dry, inert reaction medium such as pyridine or xylene. For methods B and C the process is carried out under reaction conditions suitable for the preparation of tertiary amines by alkylation of secondary amines. The reactants are heated in a suitable organic liquid at temperatures of about 60° C. to about 150° C. in the presence of an acid binding agent. Benzene, dimethylformamide, ethanol, acetonitrile, toluene, and n-butyl alcohol are preferred examples of the organic liquid reaction media. The preferred acid binding agent is potassium carbonate, but other inorganic and tertiary organic bases may be employed including other alkali and alkylene earth metal carbonates, bicarbonates, or hydrides, and the tertiary amines. All three methods have been adequately described by Wu, et al in the cited patents and articles listed above and these are hereby incorporated in entirety by reference.

As an example of a method variation to produce the same compounds somewhat differently, and N-substituted [4-(1-piperazinyl)butyl]glutarimide (VI) can be reacted with an appropriate pyrimidine system (VII) to yield a product of Formula I, e.g.

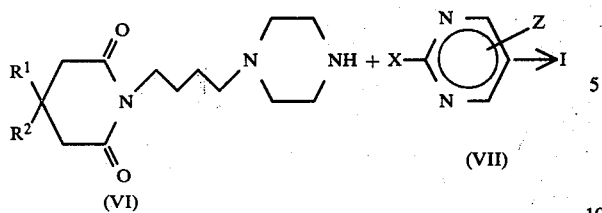

Additionally, a Formula I compound can undergo a further chemical alteration of its Z-group (e.g. hydrogenolysis of benzyloxy or hydroxy) to yield a different Formula I product.

The intermediate dialkyl glutaric acid anhydrides or imides of Formula II are commercially available, found in the chemical literature, or described herein. The general synthesis of these compounds is illustrated in Scheme 1.

Scheme 1

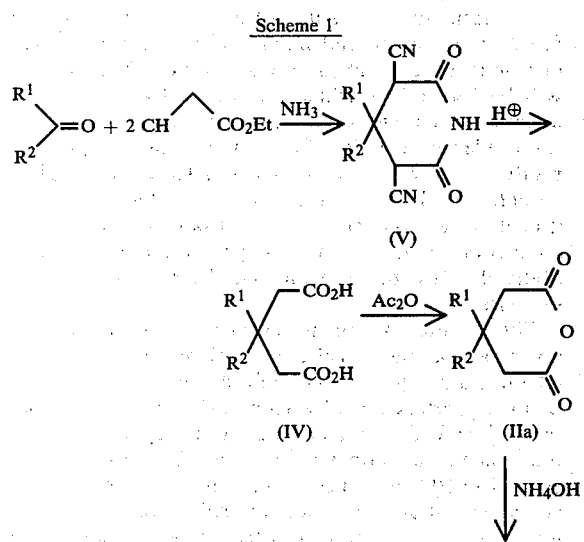

-continued
Scheme 1

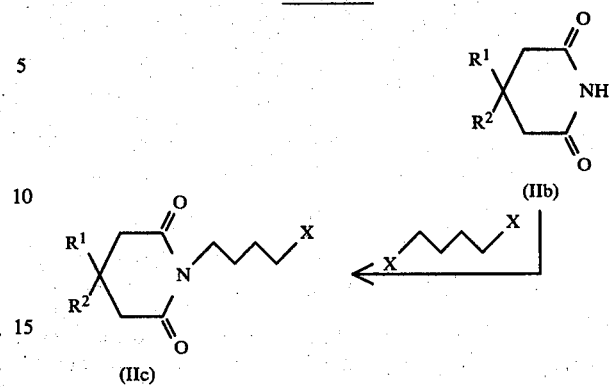

In the above scheme, $R^1$, $R^2$ and X are the same as defined hereinabove. The general synthesis is carried out by stirring a chilled mixture of 1 equivalent of the ketone with 2 equivalents of ethylcyanoacetate in an inert organic solvent containing dissolved gaseous ammonia. After stirring the chilled reaction mixture for 24 to 48 hours, the 2,4-dicyanoglutarimide product (V) is obtained and is hydrolyzed in strong mineral acid to the dicarboxylic acid product (IV). Dehydration with acetic anhydride yields the dialkylglutaric acid anhydride (IIa) which in turn can be converted to the dialkylglutarimide (IIb) by treating with ammonium hydroxide under dehydrating conditions. The N-substituted glutarimide (IIc) is readily obtained by treating (IIb) with an appropriate 1,4-disubstituted butane, e.g. 1,4-dibromobutane.

The piperazine intermediates (III) are described in the aforementioned Wu, et al patents and certain references cited therein. Although these procedures are applicable to the preparation of other piperazine intermediates not specifically disclosed therein but which are required as intermediates for the present invention, a representative synthesis of IIIc is given as a working example for further exemplification. Intermediates IIIa and IIIb are readily obtainable from IIIc using the standard methods shown by Wu, et al.

Model Synthesis of (IIIc)

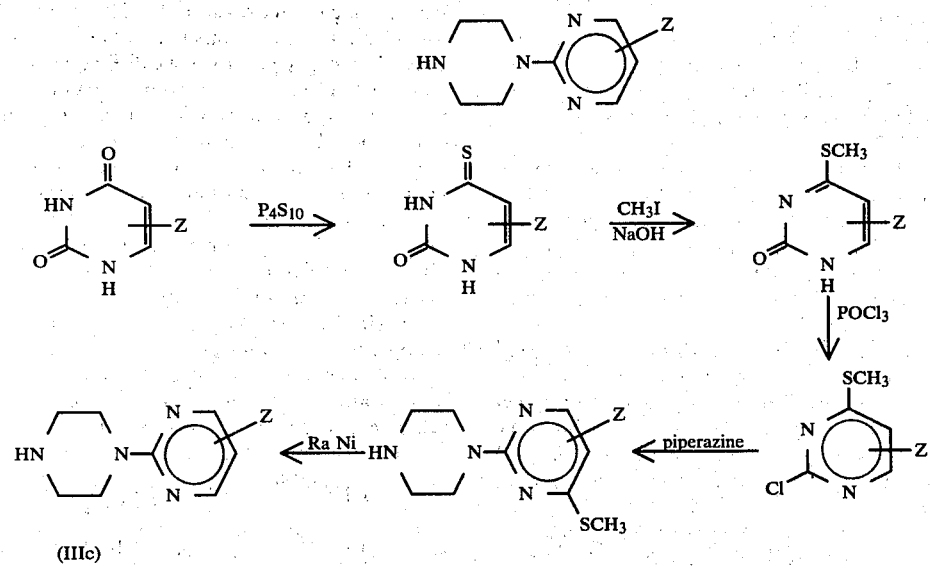

-continued
Model Synthesis of (IIIc)

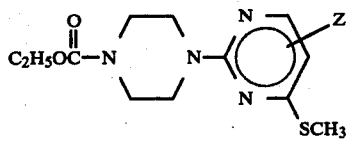 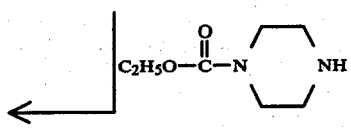

This synthetic scheme begins with a commercially available Z-substituted uracil and proceeds by known reactions to the desired piperazine intermediate. Although the route via carbethoxypiperazine is more involved, the higher yield of IIIc without by-products makes it preferred.

The formula (I) compounds are useful psychotropic agents which exhibit selective anxiolytic action. In particular, these improved compounds appear to offer an advantage over buspirone and its close analogs in that antipsychotic or neuroleptic action, with its potential adverse side effects, appears markedly reduced or absent. This realizes one objective of the instant invention, i.e., to increase selectively for this class of anxiolytic agents. Various in vivo and in vitro animal tests confirm that while the formula (I) compounds exhibit little antipsychotic activity, they otherwise retain the novel anxioselective profile exhibited by buspirone and its close analogs.

In general, antipsychotic agents are believed to act via postsynaptic dopamine receptor antagonism in the brain. Antipsychotic drugs have varying degrees of side effects which are generally extensions of the pharmacological effects particular to that class of drugs. Some specific examples of side effects possessed by antipsychotic drugs as a class are: sedation, extrapyramidal reactions (acute torsion dystonia, akathisia, Parkinsonism, tardive dyskinesias), autonomic nervous system effects.

The following screening tests were utilized as the basis to determine the anxiolytic selective profile of the instant compounds. These tests comprise:

1. Conditioned avoidance response in fasted rats treated orally. These data were obtained by the methods described in the Wu, et al. patents and publications described hereinabove.
2. Dopamine receptor binding assay reflecting antipsychotic activity (Burt, Crease, and Synder, *Molecular Pharmacology*, 12:800 (1976); Burt, Crease, and Synder, *Science*, 196:326 (1977); Crease, Burt, and Snyder, *Science*, 192:481 (1976).
3. Apomorphine stereotype behavior test in non-fasted rats which determines the ability of centrally active compounds to block apomorphine induced stereotype behavior. This preclinical test is an indication of blockade of post-synaptic dopamine receptors and potential antipsychotic efficacy (Janssen, et al., Arzneimittel-Forsch., 17:841 (1966)).

The compounds of the present invention show good activity in test 1 above and this is indicative of anxiolytic and/or antipsychotic action without pronounced sedative effects. The instant compounds exhibit very low levels of activity in tests 2 and 3, as described above, indicating a decreased antipsychotic component of pharmacological activity.

According to the pharmacological profile established by the aforementioned tests, these compounds of Formula (I) have promising potential as selective anxiolytic agents. Thus, another aspect of the instant invention concerns a process for ameliorating an anxiety state in a mammal in need of such treatment which comprises systemic administration to said mammal of an effective dose of about 0.01 to 40 mg/kg body weight of a formula (I) compound or a pharmaceutically acceptable acid addition salt thereof.

The term systemic administration as used herein refers to oral, rectal, and parenteral (i.e., intramuscular, intravenous, and subcutaneous) routes. Generally, it will be found that when a compound of the present invention is administered orally, which is the preferred route; a larger quantity of the active agent is required to produce the same effect as a smaller quantity given parenterally. In accordance with good clinical practice, it is preferred to administer the instant compounds at a concentration level that will produce effective anxiolytic effects without causing any harmful or untoward side effects.

Therapeutically, the instant compounds are generally given as pharmaceutical compositions comprised of an effective anxiolytic amount of a compound of Formula (I) or a pharmaceutically acceptable acid addition salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs and aqueous solutions.

Preferred oral compositions are in the form of tablets or capsules and may contain conventional excipients such as binding agents (e.g. syrup, acacia, gelatin, sorbitol, tragecanth, or polyvinyl pyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch), and wetting agents (e.g. sodium lauryl sulfate). Solutions or suspension or a Formula (I) compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethyleneglycols or mixtures thereof. The polyethyleneglycols consist of a mixture of non-volatile, normally liquid, polyethyleneglycols which are soluble in both water and organic liquids and which have molecular weights from about 200 to 1500.

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in °C. when not specified.

Synthesis of Intermediates

A. Intermediates of Formula II

EXAMPLE 1

3-Methyl-3-n-propylglutaric Acid Anhydride (IIa)

(a) 2,4-dicyano-3-methyl-3-n-propylglutarimide V

A mixture of 107.8 g (1.25 moles) of 2-pentanone, 282.8 g (2.5 moles) of ethyl cyanoacetate and 650 mL of anhydrous ethanol containing approximately 45 g of dissolved ammonia gas was stirred for 48 hr while being kept at 0° C. The crude product was removed by filtration, redissolved in hot water and acidified with conc. HCl resulting in precipitation of a white solid which was isolated by filtration to give 218.7 g (80%) of material which, upon recrystallization from ethanol, had a melting point of 204°–205° C.

(b) 3-Methyl-3-n-propylglutaric Acid (IV)

The glutarimide (V); (225 g, 1.02 moles) was added in portions to 480 mL conc. $H_2SO_4$. The resulting orange solution was stirred for 12 hr and then diluted by the slow addition of 420 mL $H_2O$. Carbon dioxide evolution began immediately. Following completion of the addition of water, the mixture was *gradually heated*, to minimize excessive foaming, up to reflux. Gas evolution ceased after 5 hr of reflux and the reaction mixture was diluted with 1 L water, saturated with NaCl, and extracted three times with 600 mL portions of ether. The ether extracts were dried ($Na_2SO_4$), filtered and concentrated to a residual yellow syrup which solidified to give 88 g of the crude diacid product, melting point 90°–92° C.

A 70 g (0.37 mole) portion of this crude glutaric acid (IV) was dissolved in 110 mL of acetic anhydride and gently refluxed for a period of 4 hr. The solution was concentrated to a dark oil which was distilled to give 53.2 g (84.5%) of colorless syrup, boiling point 111° at 0.1 mm. Upon standing, the anhydride (IIa) crystallized to a white solid.

EXAMPLE 2

3-Methyl-3-n-propylglutarimide (IIb)

A 10 g (0.06 mole) quantity of the anhydride prepared in Example 1 was added in small portions to 120 mL conc. $NH_4OH$. After the addition was completed, the mixture was heated to a gentle reflux and stirred for 4 hr. Upon cooling the reaction mixture, a yellow oil precipitated which solidified to a glass. Crystallization of the glass from isopropyl alcohol gave 8 g (80%) of crude product, m.p. 110°–120° C. (literature m.p. 115°–116°, Cf: N. S. Benica and C. O. Wilson, *J. Am. Pharm. Assoc.*, 39, page 451–454 (1950)).

EXAMPLE 3

N-(4-Bromobutyl)-3-methyl-3-n-propylglutarimide (IIc)

A mixture of the IIb product prepared in Example 2 (25 g; 0.15 mole), 1,4-dibromobutane (33.5 g; 0.15 mole), and $K_2CO_3$ (40.6 g; 0.29 mole) was stirred for a period of 16 hrs in 250 mL refluxing acetonitrile. The inorganic solid was removed by filtration and the filtrate was concentrated to an oil which was distilled to give 42.5 g (95%) of a light yellow oil, b.p. 165°–190° at 0.09 mm.

B. Intermediates of Formula III

EXAMPLE 4

1-(4-Aminobutyl)-4-(2-pyrimidyl)piperazine (IIIa)

4-[4-(2-Pyrimidinyl)-1-piperazinyl]butyronitrile (115.7 g; 0.5 mole) was dissolved in 1.5 L isopropyl alcohol. Approximately 50 mL of a suspension of Raney nickel in anhydrous ethanol was added and the resulting reaction mixture was heated to reflux and hydrazine (120 g) was slowly added dropwise. On completion of the reaction, the spent catalyst was removed by filtration and the filtrate was concentrated in vacuo to a yellow oil which was distilled to yield 80.1 g (60%) of product, boiling point 135°–145° C. at 0.10 mm. (The nitrile used in this reaction is described in Wu, et al., *Journal of Medicinal Chemistry*, 15, page 477–479 (1972).)

EXAMPLE 5

8-(2-Pyrimidinyl)-8-aza-5-azoniaspiro[4.5]decane Bromide (IIIb')

A mixture of 1-(2-pyrimidinyl)piperazine (32.8 g; 0.2 mole), 1,4-dibromobutane (108 g; 0.5 mole) and finely powdered sodium carbonate (21.2 g, 0.2 mole) in 400 mL isopropanol was stirred and refluxed for a 16 hr period. The hot reaction mixture was filtered and the filtrate, on standing at room temperature, provided 50.3 g (84% yield) of product. Crystallization of this material from isopropanol affords analytically pure product, m.p. 241.5°–242.5° C. (corr.).

Anal. Calcd. for $C_{12}H_{19}N_4 \cdot Br$: C, 48.17; H, 6.40; N, 18.72; Br, 26.71. Found: C, 48.39; H, 6.53; N, 18.64; Br, 26.60.

The open chain intermediate, 1-(4-bromobutyl)-4-(2-pyrimidinyl)piperazine (IIIb), can be synthesized according to methods described by Wu, et al, U.S. Pat. No. 3,717,634 or Pollard, et al., *Journal of Organic Chemistry*, Vol. 24, page 764–7 (1959).

EXAMPLE 6

1-(5-Fluoro-2-pyrimidinyl)piperazine (IIIc)

(a) 1-Carbethoxy-4-(5-fluoro-4-methylthio-2-pyrimidinyl)piperazine

A mixture of 2-chloro-5-fluoro-4-methylthio-2-pyrimidine (5.5 g; 0.03 mole); N-carbethoxypiperazine (4.9 g; 0.03 mole); $K_2CO_3$ (12.7 g; 0.09 mole of finely divided material); KI (approximately 0.1 g) and 150 mL of acetonitrile was refluxed for 18–20 hr. The reaction was filtered while hot and the filtrate was concentrated to a residue which was crystallized in ethanol to yield 6.7 g (72.5%) of product, m.p. 110°–112° C.

(b) 5-Fluoro-2-(4-carbethoxy-1-piperazinyl)pyrimidine

A mixture of 5.25 g (0.017 mole) of the product prepared above in (a) and a teaspoon full of wet Raney nickel in 100 mL ethanol was refluxed for at least 12 hr. The nickel catalyst was removed by filtration and the filtrate was recrystallized from ethanol to give a 62% yield of material, m.p. 100°–102° C.

A 3.1 g (0.012 mole) portion of the carbethoxypiperazine intermediate prepared in (b) above, was dissolved in a 10% ethanolic KOH solution (5 g KOH in 50 mL 95% ethanol) and the solution was refluxed for 6-8 hr. Filtration removed the solid which had formed during reflux and the filtrate was concentrated to a residue. The residue was taken up in 100 ml of Et$_2$O and washed with water. The Et$_2$O layer was dried (MgSO$_4$), filtered, and concentrated to 1.9 g of residual light oil. The oil was treated with ethanolic HCl to yield 1.6 g (61.5%) of the hydrochloride salt of 1-(5-fluoro-2-pyrimidinyl)piperazine, m.p. 250°–252° C. (dec.).

SYNTHESIS OF PRODUCTS (I)

Method A

EXAMPLE 7

4,4-Dimethyl-1-[4-[4-(2-pyrimidinyl)-1-piperazinyl]-butyl]-2,6-piperazinedione Hydrochloride A solution of 3,3-dimethylglutaric anhydride (17.1 g; 0.12 mole) and 1-(4-aminobutyl)-4-(2-pyrimidinyl)piperazine (28.2 g; 0.12 mole) in 200 mL xylene was refluxed for 20 hr collecting water of reaction by means of a Dean Stark trap. The reaction mixture was filtered while warm (approximately 80° C.) and the filtrate was concentrated in vacuo to give 47.2 g of residue. Distillation of the residue yielded 31.8 g of base, b.p. 210°–230° C./0.01 mm. The distilled product could either be crystallized from acetonitrile to give solid base, melting approximately 97°–99° C. or could be treated with ethanolic HCl to give the hydrochloride salt, m.p. 203°–205° C.

Anal. Calcd. for C$_{19}$H$_{29}$N$_5$Cl$_2$.HCl: C, 57.64; H, 7.64; N, 17.69. Found: C, 57.59; H, 7.48; N, 17.58.

NRM (DMSO-d$_6$): 1.00 (6,s); 1.60 (4,m); 2.56 (4,s); 3.09 (4,m); 3.55 (6,m); 4.67 (2,bd [13.3 Hz]); 6.75 (1,t [4.6 Hz]); 8.45 (2,d [4.6 Hz]); 11.70 (1,bs).

IR (KBr): 1120, 1360, 1450, 1555, 1587, 1670, 1720, 2450, and 2960 cm$^{-1}$.

In this and the other examples which follow, melting points, unless specified otherwise, are uncorrected. The nuclear magnetic resonance (NMR) spectral characteristics refer to chemical shifts ( ) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m), doublet (d), triplet (t), quartet (q), or doublet of doublets (dd). Coupling intervals in Hz resulting from peak splitting by adjacent protons are given in brackets. Abbreviations employed are DMSO-d$_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

Method B

EXAMPLE 8

4-Ethyl-4-methyl-1-[4-[4-(2-pyrimidinyl-1-piperazinyl]-butyl]-2,6-piperidinedione Hydrochloride A mixture of 4-ethyl-4-methylglutarimide (2.5 g; 0.016 mole), 1-(2-pyrimidinyl)-4-spiropiperazine quaternary salt (4.8 g; 0.016 mole), prepared in example 5, and K$_2$CO$_3$ (2.6 g, 0.019 mole) was stirred in 150 mL dimethylformamide for 12–16 hr at 150° C. The cooled reaction mixture was filtered and the filtrate was concentrated in vacuo to a residue which was taken up in chloroform and washed with two 250 mL portions of water. The chloroform extract was dried (Na$_2$SO$_4$) and concentrated to a gummy residue which was dissolved in a minimum amount of acetonitrile and treated with 2.6 mL of 6.15 N ethanolic HCl. The hydrochloride salt was obtained by filtration to yield 4.9 g (75% yield) of white solid. Recrystallization from acetonitrile gave material, m.p. 195°–197° C.

Anal. Calcd. for C$_{20}$H$_{31}$N$_5$O$_2$.HCl: C, 58.60; H, 7,87; N, 17.08. Found: C, 58.42; H, 7.81; N, 17.25.

NMR (DMSO-d$_6$): 0.81 (3,t [7.2 Hz]); 0.93 (3,s); 1.32 (2,q [7.2 Hz]); 1.61 (4,m); 2.54 (4,s); 3.07 (4,m); 3.55 (6,m); 4.67 (2,bd [13.0 Hz]); 6.73 (1,t [4.5 Hz]); 8.44 (2,d [4.5 Hz]); 11.90 (1,bs).

IR (KBr): 1120, 1365, 1445, 1480, 1555, 1590. 1670, 1720, 2450, and 2960 cm$^{-1}$.

Method C

EXAMPLE 9

4-Methyl-4-propyl-1-[4-[4-(2-pyrimidinyl)-1-piperazinyl]butyl]-2,6-piperidinedione Dihydrochloride A mixture of N-(4-bromobutyl)-3-methyl-3-n-propylglutarimide [prepared in Example 3] (5 g; 0.016 mole), 1-(2-pyrimidinyl)piperazine (2.62 g; 0.016 mole), K$_2$CO$_3$ (6.6 g; 0.048 mole) and KI (0.5 g) was stirred in 200 mL refluxing acetonitrile for approximately 18 hrs. The reaction mixture was filtered and concentrated in vacuo to a residual oil which was partitioned between CHCl$_3$ and water. The CHCl$_3$ layer was dried (MgSO$_4$), filtered, and concentrated to an oil which was purified as the HCl salt by recrystallization from isopropyl alcohol. A total of 5 g of white solid, m.p. 188°–204° C., was obtained.

Anal. Calcd. for C$_{21}$H$_{33}$N$_5$O$_2$.2HCl: C, 54.79; H, 7.67; N, 15.22. Found: C, 54.93; H, 7.69; N, 14.96.

NMR (DMSO-d$_6$): 0.86 (3,m); 0.94 (3,s); 1.24 (2,m); 1.55 (6,m); 2.54 (4,s); 3.09 (4,m); 3,60 (6,m); 4.71 (2,bd [13.0]); 6.81 (1,t [4.9]); 8.50 (2,d [4.9]). 11.80 (2,bs).

IR (KBr) 1117, 1350, 1435, 1540, 1585, 1620, 1670, 1718, 2580, and 2960 cm$^{-1}$.

EXAMPLE 10

4,4-Diethyl-1-[4-[4-(2-pyrimidinyl)-1-piperazinyl]-butyl]-2,6-piperidinedione Dihydrochloride Using the procedure outlined in Example 9 but starting with N-(4-bromobutyl)-3,3-diethylglutarimidine as the IIc component, a tan colored hydrochloride salt, m.p. 181°–203° C. was obtained.

Anal. Calcd. for C$_{21}$H$_{33}$N$_5$O$_2$.2HCl: C, 54.78; H, 7.66; N, 15.21. Found: C, 54.77; H, 7.74; N, 14.85.

NMR (DMSO-d$_6$): 0.77 (6,t [7.3]); 1.31 (4,q [7.3]); 1.62 (4,m); 2.55 (4,s); 3.08 (4,m); 3.59 (6,m); 4.71 (2,bd [13.0]); 6.81 (1,t [4.9]); 8.50 (2,d [4.9]); 9.30 (1,bs); 9.70 (1,bs).

IR (KBr): 1118, 1355, 1440, 1550, 1620, 1670, 1720, 2440, and 2970 cm$^{-1}$.

EXAMPLE 11

4,4-Dimethyl-1-[4-[4-(5-fluoro-2-pyrimidinyl)-1-piperazinyl]butyl]-2,6-piperidinedione Hydrochloride Equimolar amounts of N-(4-bromobutyl)-3,3-dimethylglutarimide and 1-(5-fluoro-2-pyrimidinyl)piperazine [prepared in Example 6] were reacted using the procedure outlined in Example 9. The hydrochloride salt was obtained as a white solid, m.p. 241°–243° C.

Anal. Calcd. for $C_{19}H_{28}FN_5O_2 \cdot HCl$: C, 55.14; H, 7.07; N, 16.92. Found: C, 54.86; H, 7.08; N, 16.58.

NMR (DMSO-$d_6$): 0.98 (6,s); 1.60 (4,m); 2.54 (4,s); 3.07 (4,m); 3.52 (6,m); 4.56 (2,bd [13.2]); 8.51 (2,s); 11.75 (1,bs).

IR (KBr): 1115, 1250, 1350, 1490, 1560, 1610, 1670, 1720, 2600, and 2960 cm$^{-1}$.

EXAMPLE 12

4,4-Dimethyl-1-[4-[4-(5-hydroxy-2-pyrimidinyl)-1-piperazinyl]butyl]-2,6-piperidinediode (a) 2-Methylsulfonyl-5-phenylmethoxypyrimidine A solution of 2-methylthio-5-phenylmethoxypyrimidine (Cf: Chesterfield, et al., *J. Chem. Soc.*, 1960, 4590; D. T. Hurst, et al., *J. Chem. Soc.*, 1965, 7116) (2.72 g, 0.012 mole) in 25 mL CHCl$_3$ was added dropwise to m-chloroperbenzoic acid (4.38 g, 0.025 mole) in CHCl$_3$. The resulting mixture was heated at reflux for 18 hr, cooled, filtered, and concentrated in vacuo. The residue was triturated with 10% NaHCO$_3$, collected by filtration, and recrystallized from ethanol to provide 2.1 g (68%) off white solid, m.p. 100°–102° C.

(b) 5-Phenylmethoxy-2-(1-piperazinyl)pyrimidine

A mixture of the pyrimidine prepared in (a) above (24.5 g, 0.09 mole), piperazine (77.5 g, 0.9 mole), and toluene (160 mL) was heated at 150° C. in a stainless steel omb for 22 hr. The reaction mixture was filtered, concentrated in vacuo, and the residue crystallized from Skelly B to give 10.15 g (42%) off-white solid, m.p. 94°–97° C.

(c) 4,4-Dimethyl-1-[4-[4-(5-phenylmethoxy-2-pyrimidinyl)-1-piperazinyl]butyl]-2,6-piperidinedione Equimolar amounts of N-(4-bromobutyl)-3,3-dimethylglutarimide and the piperazinyl pyrimidine prepared in (b) above can be reacted using the procedure outlined in Example 9. Filtration of the hot reaction mixture and concentration in vacuo of the filtrate will give a residue which can be dissolved in CHCl$_3$, washed with water, dried (MgSO$_4$), and evaporated. The crude material can be recrystallized from Skelly B to yield the product in its base form.

This phenylmethoxy derivative can undergo hydrogenolysis by shaking a mixture of 10 g of the base, 1 g 10% Pd on carbon in 200 mL ethanol at 50° C. under H$_2$ for 10–30 min. The reaction mixture can be filtered and the filtrate concentrated in vacuo and the residue recrystallized from acetonitrile to provide the desired 5-hydroxy product.

The following products of Formula I can be prepared using the appropriate glutarimide (IIc) and pyrimidinylpiperazine (IIIc) following the procedure of Example 9.

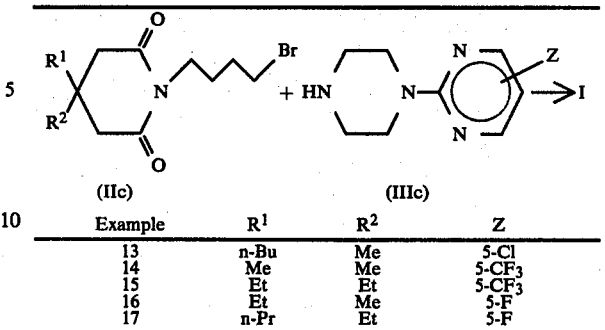

| Example | $R^1$ | $R^2$ | Z |
|---|---|---|---|
| 13 | n-Bu | Me | 5-Cl |
| 14 | Me | Me | 5-CF$_3$ |
| 15 | Et | Et | 5-CF$_3$ |
| 16 | Et | Me | 5-F |
| 17 | n-Pr | Et | 5-F |

What is claimed is:

1. A compound selected from the group consisting of a compound having Formula (I)

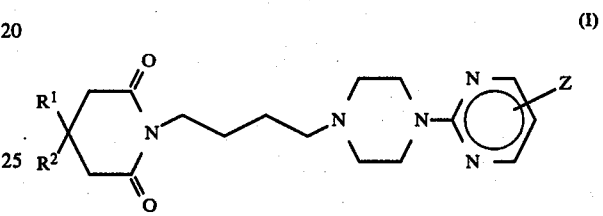

wherein $R^1$ and $R^2$ are independently selected from $C_1$ to $C_4$ alkyl groups; with Z being hydrogen, hydroxyl, halogen, or trifluoromethyl;

and the non-toxic pharmaceutically acceptable acid addition salts thereof.

2. A compound of claim 1 wherein Z is 5-fluoro.
3. A compound of claim 1 wherein Z is 5-hydroxy.
4. The compound of claim 1, 4,4-dimethyl-1-[4-[4-(2-pyrimidinyl)-1-piperazinyl]butyl]-2,6-piperidinedione or a pharmaceutically acceptable acid addition salt thereof.
5. The compound of claim 1, 4-ethyl-4-methyl-1-[4-[4-(2-pyrimidinyl)-1-piperazinyl]butyl]-2,6-piperidinedione or a pharmaceutically acceptable acid addition salt thereof.
6. The compound of claim 1, 4,4-diethyl-1-[4-[4-(2-pyrimidinyl)-1-piperazinyl]butyl]-2,6-piperidinedione or a pharmaceutically acceptable acid addition salt thereof.
7. The compound of claim 1, 4-methyl-4-propyl-1-[4-[4-(2-pyrimidinyl)-1-piperazinyl]butyl]-2,6-piperidinedione or pharmaceutically acceptable acid addition salt thereof.
8. The compound of claim 1, 4,4-dimethyl-1-[4-[4-(5-fluoro-2-pyrimidinyl)-1-piperazinyl]butyl]-2,6-piperidinedione or a pharmaceutically acceptable acid addition salt thereof.
9. The process for ameliorating an undesirable anxiety state in a manual comprising systemic administration to said mammal of an effective anxiolytic dose of from 0.01 to 40 mg/kg body weight of a compound claimed in claim 1.
10. The process of claim 9 wherein the Formula (I) compound is 4,4-dimethyl-1-[4-[4-(2-pyrimidinyl)-1-piperazinyl]butyl]-2,6-piperidinedione or a pharmaceutically acceptable acid addition salt thereof.
11. A pharmaceutical composition in dosage unit form suitable for systemic administration to a mammalian host comprising a pharmaceutical carrier and an amount of a compound claimed in claim 1 to provide an effective non-toxic dose of from 0.01 to 40 mg/kg body weight of said host.
12. The pharmaceutical composition of claim 11 wherein the Formula (I) compound is 4,4-dimethyl-1-[4-[4-(2-pyrimidinyl)-1-piperazinyl]butyl]-2,6-piperidinedione or a pharmaceutically acceptable acid addition salt thereof.

* * * * *